US00PP28615P2

(12) United States Plant Patent
Park

(10) Patent No.: US PP28,615 P2
(45) Date of Patent: Nov. 7, 2017

(54) ***COREOPSIS* PLANT NAMED 'URIGS01'**

(50) Latin Name: ***Coreopsis grandiflora*×*Coreopsis verticillata***
Varietal Denomination: URIGS01

(71) Applicant: Uriseed Institute, Icheon-si (KR)

(72) Inventor: Kong Young Park, Icheon-si (KR)

(73) Assignee: URISEED INSTITUTE, Icheon-si, Gyeonggi-Do (KR)

( * ) Notice: Subject to any disclaimer, the term of this patent is extended or adjusted under 35 U.S.C. 154(b) by 122 days.

(21) Appl. No.: 14/757,218

(22) Filed: Dec. 7, 2015

(51) Int. Cl.
*A01H 5/02* (2006.01)

(52) U.S. Cl.
USPC ..... Plt./417

(58) Field of Classification Search
USPC ..... Plt./263.1, 417
See application file for complete search history.

(56) References Cited

U.S. PATENT DOCUMENTS

PP22,565 P2 * 3/2012 Dobres ..... A01H 5/00

OTHER PUBLICATIONS

Park et al. 2014. "Development of a New *Coreopsis* variety 'Uridream Pink' by Gamma-ray irradiation." Kor. J. Hort. Sci Technol. 32(6): 906-911. 6 pages.*

* cited by examiner

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of hybrid *Coreopsis* plant named, 'URIGS01', that is characterized by its inflorescences with ray florets that are dark orange-yellow in color with yellow margins, its relatively small leaves, its relatively small inflorescences, and its compact, densely branched plant habit.

2 Drawing Sheets

Botanical classification: *Coreopsis grandiflora*×*Coreopsis verticillata.*
Variety denomination: 'URIGS01'.

BACKGROUND OF THE INVENTION

The present invention relates to a new and distinct cultivar of *Coreopsis* plant, botanically an interspecific hybrid between *Coreopsis grandiflora*×*Coreopsis verticillata*, known as *Coreopsis* 'URIGS01' and will be referred to hereinafter by its cultivar name, 'URIGS01'. The new cultivar of *Coreopsis* is an herbaceous perennial grown for landscape and container use.

The new cultivar arose from an ongoing breeding conducted program by the Inventor in Icheon-si, Korea. The objective for this new cultivar was to produce a new cultivar with orange colored inflorescences.

The new cultivar arose from gamma irradiation of unrooted cuttings of *Coreopsis* 'Crème Brulee' (U.S. Plant Pat. No. 16,096) in 2011. 'URIGS01' was selected as a single unique plant from amongst the 500 seedlings that were evaluated from the resulting seedlings in 2012.

Asexual propagation of the new cultivar was first accomplished by stem cuttings by the Inventor in 2012. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'URIGS01' as unique cultivar of *Coreopsis*.

1. 'URIGS01' exhibits inflorescences with ray florets that are dark orange-yellow in color yellow margins.
2. 'URIGS01' exhibits small leaves.
3. 'URIGS01' exhibits relatively small inflorescences.
4. 'URIGS01' exhibits a compact, densely branched plant habit.

The parent plant of 'URIGS01', 'Crème Breulee', differs from 'URIGS01' in having larger a larger plant size and inflorescences that are larger and yellow in color. 'URIGS01' can be compared to *Coreopsis* cultivars 'Novcorar' (U.S. Plant Pat. No. 22,565) and 'Sienna Sunset' (U.S. Plant Pat. No. 20,470). Both are similar to 'URIGS01' in inflorescence coloration. 'Novcorar' differs from 'URIGS01' in having inflorescences that are lighter in color and in lacking yellow margins on its ray florets. 'Sienna Sunset' differs from 'URIGS01' in having larger inflorescences that are lighter orange-yellow in color.

BRIEF DESCRIPTION OF THE DRAWINGS

The accompanying colored photographs illustrate the overall appearance and distinct characteristics of the new *Coreopsis*. The photographs were taken of a one year-old plant of 'URIGS01' as grown outdoors in a 17-cm container in Boskoop, The Netherlands.

The photograph in FIG. 1 provides a side view of a plant of 'URIGS01' in bloom.

Figure 1:
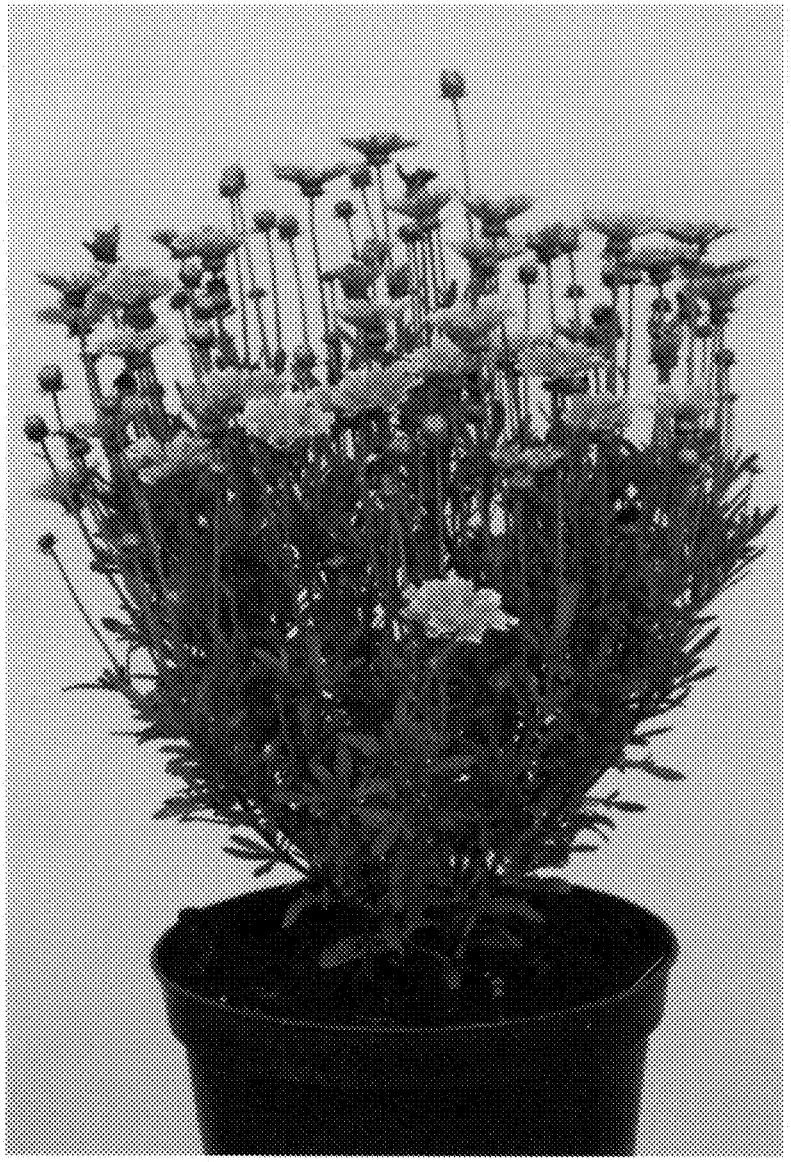
Figure 2:
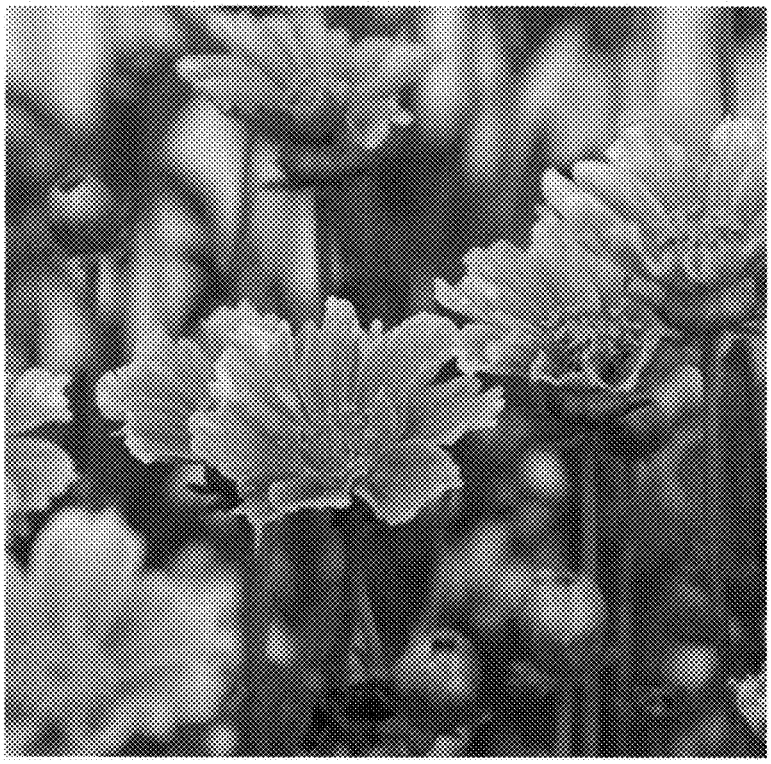

The photograph in FIG. 2 provides a close-up view of the inflorescences of 'URIGS01'.

Figure 3:
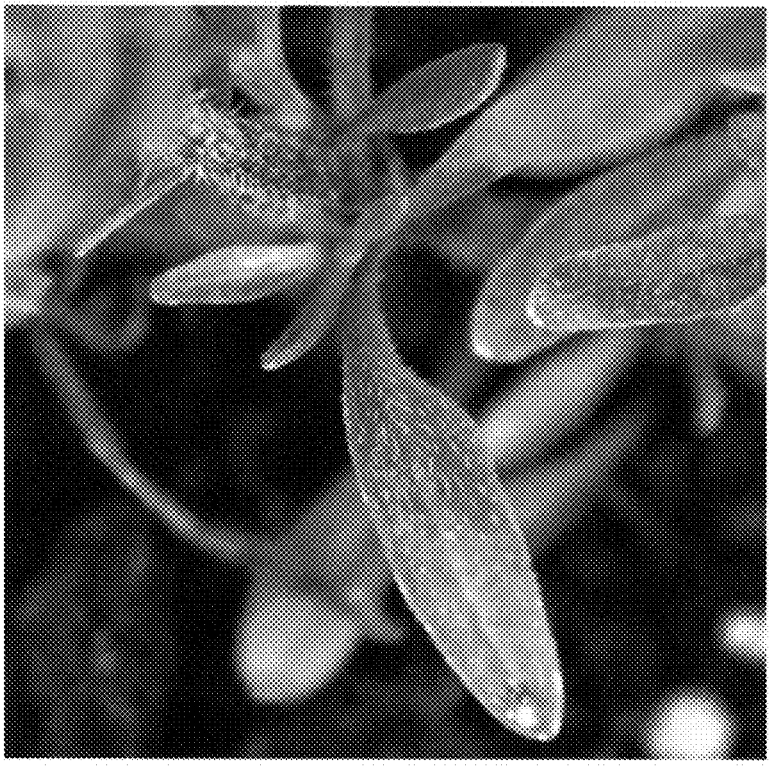

The photograph in FIG. 3 provides a close-up view of the foliage of 'URIGS01'.

The colors in the photographs may differ slightly from the color values cited in the detailed botanical description, which accurately describes the colors of the new *Coreopsis*.

DETAILED BOTANICAL DESCRIPTION

The following is a detailed description of one year-old plants of the new cultivar as grown outdoors in 17-cm containers in Boskoop, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Early summer to late summer in The Netherlands.

*Plant type*.—Herbaceous perennial.

*Plant habit*.—Clump-forming, upright, compact and densely branched.

*Height and spread*.—An average of 29.4 cm in height and 25.5 cm in width.

*Cold hardiness*.—At least to U.S.D.A Zone 4.

*Diseases resistance*.—Has been observed to be highly resistant to powdery mildew and leaf spot.

*Root description*.—Fibrous when young, becoming fleshy with age.

*Propagation*.—Terminal stem cuttings.

*Root development*.—Roots initiate in 6 to 8 days and fully develop in a 128-cell plug in about 1 month.

*Growth rate*.—Moderate.

Stem description:

*Shape*.—Rounded.

*Stem color*.—144A.

*Stem size*.—An average of 5.8 cm in length (excluding inflorescence) and 2 mm in diameter.

*Stem surface*.—Glabrous, moderately glossy, and slightly axially ribbed.

*Stem aspect*.—Upward.

*Stem strength*.—Strong.

*Branching habit*.—Well-branched, an average of 210 lateral branches.

*Internode length*.—An average of 1.3 cm.

Foliage description:

*Leaf division*.—Simple.

*Leaf margins*.—Entire.

*Leaf size*.—Hastate leaves; an average of 2.5 cm in length and 1.1 cm in width, lanceolate leaves; an average of 2.4 cm in length and 4.5 mm in width.

*Leaf shape*.—Hastate to lanceolate.

*Leaf base*.—Long cuneate.

*Leaf apex*.—Broadly acute.

*Leaf venation*.—Pinnate, color; upper and lower surfaces; 144A.

*Leaf attachment*.—Sessile.

*Leaf arrangement*.—Opposite.

*Leaf surface*.—Both surfaces moderately pubescent with very short soft hairs and average of 0.75 mm in length and 155D in color.

*Leaf color*.—Young upper and lower surfaces; 137B, mature upper and lower surfaces; 137A.

*Leaf number*.—An average of 10 leaves (5 pairs) per stem.

Inflorescence description:

*Inflorescence type*.—Terminal capitulate, with a single row of ray florets surrounding disk florets in the center.

*Lastingness of inflorescence*.—An average of 3 weeks, self-cleaning.

*Fragrance*.—Moderate to faint, of musk and straw.

*Quantity of inflorescences*.—An average of 1 per lateral branch.

*Inflorescence size*.—An average of 3.1 cm in diameter and 1 cm in height, disk portion an average of 9 mm in diameter.

*Inflorescence buds*.—An average of 5 mm in depth and 6 mm in diameter, flattened globular in shape, color; 146B with apex 153A.

*Peduncle*.—An average of 8.4 cm in length and 1 mm in width, held straight upright, slightly glossy and glabrous surface, N144A to N144C in color and moderately strong.

Involucral bracts:

*Bract number*.—Two rows of 8.

*Bract arrangement*.—Rotate, placed in two separate rows.

*Bract size*.—Outer bracts; an average of 4 mm in length and 2 mm in width, inner bracts; an average of 7 mm in length and 4.5 mm in width.

*Bract color*.—Inner bracts; 153A to 153B with base 144A and outer bracts; 143A.

*Bract surface texture*.—Glabrous and slightly glossy on upper and lower surfaces of outer and inner bracts.

*Bract apex*.—Outer bracts; obtuse and inner bracts; acute.

*Bract base*.—Broadly cuneate on inner and outer bracts.

*Bract margins*.—Entire.

*Bract shape*.—Outer bracts; oblong, inner bracts; ovate.

Ray florets (sterile):

*Number*.—An average of 8 arranged primarily in one row.

*Shape*.—Obcordate.

*Size*.—An average of 1.5 cm in length and 1 mm in width.

*Apex*.—Irregularly lobed with an average of 4 acute lobes, lobes are acute.

*Base*.—Cuneate.

*Margins*.—Entire with apex lobed.

*Aspect*.—Held upward at an average angle of 25° to horizontal.

*Surface texture*.—Glabrous and velvety on both surfaces.

*Color*.—Upper surface when opening; 179A with narrow margins 8A and base 9A, lower surface when opening; 166A with narrow margins 8B and base 9B, upper surface when fully open; 172A to 172B with narrow margins 8B and base 9A, lower surface when fully open; 165B with narrow margins 8B and base 9B, color not fading.

Disk flowers (perfect):

*Shape*.—Tubular, spirally arranged on disc.

*Apex*.—Acute.

*Base*.—Lower 66% fused into tube.

*Number*.—About 50.

*Size*.—An average of 5 mm in length and 2 mm in width at the apex and 0.5 mm in width at the base.

*Color*.—En masse; 13A, corolla; 13C with base of tube 151C in color, flared portion is 13A.

*Receptacle*.—An average of 4 mm in diameter and 2 mm depth, 144C in color.

Reproductive organs:

*Presence*.—Disk flowers are perfect, ray flowers are sterile.

*Gynoecium*.—1 pistil, an average of 5 mm in length, style; an average of 4 mm in length and 151D in color, stigma is decurrent and 17A in color, ovary is 151C in color.

*Androcoecium*.—5 stamens, anther; basifixed and linear in shape, an average of 2 mm in length and 177A in color, pollen is low in quantity and 17B in color.

*Fruit/seed*.—No fruit or seed development was observed.

It is claimed:

1. A new and distinct cultivar of *Coreopsis* plant named 'URIGS01' as herein illustrated and described.

* * * * *